(12) United States Patent
Chiao et al.

(10) Patent No.: US 7,961,093 B2
(45) Date of Patent: Jun. 14, 2011

(54) WIRELESS SENSOR SYSTEM AND METHOD

(75) Inventors: Jung-Chih Chiao, Grand Prairie, TX (US); Lun-Chen Hsu, Arlington, TX (US)

(73) Assignee: Board of Regents, The University of Texas System, Arlington, TX (US)

( * ) Notice: Subject to any disclaimer, the term of this patent is extended or adjusted under 35 U.S.C. 154(b) by 539 days.

(21) Appl. No.: 11/836,612

(22) Filed: Aug. 9, 2007

(65) Prior Publication Data

US 2009/0040044 A1    Feb. 12, 2009

(51) Int. Cl.
    *G08B 1/08* (2006.01)
(52) U.S. Cl. ........... 340/539.26; 340/539.12; 340/572.1; 340/572.4; 340/572.7; 340/573.4; 340/575; 340/576; 600/510; 600/515; 600/516; 600/518
(58) Field of Classification Search .............. 340/539.26, 340/539.12, 572.1, 572.4, 572.7, 573.4, 575, 340/576; 600/510, 515, 516, 518
    See application file for complete search history.

(56) References Cited

U.S. PATENT DOCUMENTS

| | | | | |
|---|---|---|---|---|
| 3,972,320 A | * | 8/1976 | Kalman | 600/519 |
| 4,440,177 A | | 4/1984 | Anderson et al. | 128/719 |
| 5,297,424 A | * | 3/1994 | Sackett | 73/146.5 |
| 5,650,770 A | * | 7/1997 | Schlager et al. | 340/573.1 |
| 5,704,352 A | * | 1/1998 | Tremblay et al. | 600/300 |
| 6,330,464 B1 | | 12/2001 | Colvin, Jr. et al. | 606/316 |
| 7,215,991 B2 | * | 5/2007 | Besson et al. | 600/509 |
| 2002/0013538 A1 | | 1/2002 | Teller | 600/549 |
| 2006/0097879 A1 | * | 5/2006 | Lippincott | 340/573.1 |
| 2006/0174693 A1 | * | 8/2006 | Chen et al. | 73/29.01 |
| 2006/0238309 A1 | | 10/2006 | Takatama | 340/10.41 |
| 2007/0106172 A1 | | 5/2007 | Abreu | 600/549 |

FOREIGN PATENT DOCUMENTS

WO    2007/068002    6/2007

OTHER PUBLICATIONS

Cao, H., "An Infant Monitoring System Using $CO_2$ Sensors", *2007 IEEE RFID Conference*, pp. 1-7, (Mar. 2007).
Neuman, M.R., et al., "Cardiopulmonary monitoring at home: the CHIME monitor", *Physiol. Meas.*, vol. 22, pp. 267-286 (2001).
Hsu, Lun-Chen, et al., "Evaluation of commercial metal-oxide based $NO_2$ sensors", *Sensor Review*, vol. 27, No. 2, pp. 121-131 (2007).
"TGS 4161—for the detection of Carbon Dioxide", *FIGARO Product Information*, pp. 1-2 (Rev. 04/03).
Modi, Ashish, et al., "Miniaturized gas ionization sensors using carbon nanotubes", *Nature*, vol. 424, pp. 171-174, (Jul. 10, 2003).

(Continued)

*Primary Examiner* — Tai T Nguyen
(74) *Attorney, Agent, or Firm* — Parks IP Law LLC; Cynthia Parks, Esq.

(57) ABSTRACT

The invention is a wireless sensor system coupled with sensors to non-invasively monitor external stimuli. By monitoring the outputs of sensors, the output data can be used to activate an alarm or logged for further diagnoses of human conditions.

16 Claims, 14 Drawing Sheets

OTHER PUBLICATIONS

Singh S., et al., "Internet based infant monitoring system", *Engineering in Medicine and Biology, 1999, 21st Annual Conference and the 1999 Annual Fall Meeting of the Biomedical Engineering Society, BMES/EMBS Conference*, vol. 2, pp. 674 (Oct. 13, 1999) (Abstract only).

Dickinson, P., et al., "An FPGA-based infant monitoring system", *Field-Programmable Technology, 2005 Proceedings*, pp. 315-316, (Dec. 2005) (Abstract only).

Chou, Jack, "Hazardous Gas Monitors: A Practical Guide to Selection, Operation and Applications" (1999) (Ch. 1, Ch. 2, Ch. 4).

Hoppenbrouwers, T., et al., "Multivariable cardiorespiratory monitoring at home: collaborative home infant monitoring evaluation (CHIME)", *Engineering in Medicine and Biology Society Bridging Disciplines for Biomedicine.*, vol. 1, pp. 61-62 (1996) (Abstract only).

Linti, C., et al., "Sensory baby vest for the monitoring of infants", *International Workshop on Wearable and Implantable Body Sensor Networks*, pp. 3 (Apr. 2006) (Abstract only).

Von Maltzahn, W.W., et al., "Oxygen consumption monitor for infants", *Engineering in Medicine and Biology Society: 1994 Engineering Advances: New Opportunities for Biomedical Engineers. Proceedings of the 16th Annual International Conference of the IEEE*, vol. 2, pp. 856-857 (1994) (Abstract only).

Nguyen, Huu Minh, et al., "Development of carbon dioxide sensing system for searching victims in large scale disasters", *SICE 2004 Annual Conference*, vol. 2, pp. 1358-1361 (Aug. 2004) (Abstract only).

Bunker, J. et al., "SIDS home monitor with telecommunications capabilities", *Engineering in Medicine and Biology Society, 1993, Proceedings of the 15th Annual International Conference of the IEEE*, pp. 1061-1061 (1993) (Abstract Only).

Bilstrup, U.et al., "An architecture comparison between a wireless sensor network and an active RFID system", *Annual IEEE International Conference on Local Computer Networks*, pp. 583-584, (Nov. 16-18, 2004).

Cho, H., et al., "Design and implementation of an active RFID system platform", *In Proc. of the International Symposium on Applications and the Internet Workshops*, (Jan. 23-27, 2005) (Abstract Only).

Waldrop, J., et al., "Colorwave: an anticollision algorithm for the reader collision problem", *IEEE International Conference on Communications*, vol. 2, pp. 1206-1210, (May 11-15, 2003) (Abstract Only).

Ho, J. et al., "HiQ: a hierarchical Q-learning algorithm to solve the reader collision problem", *In Proc. of the International Symposium on Applications and the Internet Workshops*, (Jan. 23-27, 2006) (Abstract Only).

Birari, S. M., et al., "Mitigating the reader collision problem in RFID networks with mobile readers", *13th IEEE International Conference on Networks, Jointly held with 2005 IEEE 7th Malaysia International Conference on Communication*, (Nov. 16-18, 2005) (Abstract only).

Kin, S. L., et al., "The reader collision problem in RFID systems", *In Proc. of IEEE International Symposium on Microwave, Antenna, Propagation and EMC Technologies for Wireless Communications*, vol. 1, pp. 658-661, (Aug. 8-12, 2005).

Radiometrix wireless module datasheet, http://www.radiometrix.com, accessed Apr. 24, 2008.

* cited by examiner

WIRELESS SENSOR SYSTEM AND METHOD

BACKGROUND

The invention is generally a wireless sensor system, and more particularly, a monitoring system.

Healthcare cost is an urgent issue. In the U.S., the cost for healthcare has reached 16% of the Gross National Product in 2004, equating to $1.88 trillion US dollars. The costs for infant healthcare are high due to the fact that the infant healthcare is highly labor intensive. For healthy infants, Sudden Infant Death Syndrome ("SIDS") is the most critical problem needed to be addressed. SIDS is defined as any sudden and unexplained death of an apparently healthy infant aged one month to one year. According to the National SIDS/Infant Death Resource Center, in 2004, SIDS was responsible for roughly 50 deaths per 100,000 births in the U.S. Although the SIDS rate has been reducing, due to the awareness in parents and nurses, SIDS is a cost still too high for any family to suffer the loss of a newborn. Reducing the sudden death rate in infants by an effective monitoring and alarm system is a challenge for researchers.

Although the causes of SIDS have not been thoroughly explained, respiratory deficiencies have been known as the most common reason. Inborn factors such as disorders in the lungs or glands, respiratory infections, and improper sleeping positions are possible causes. SIDS may happen to healthy infants without any identifiable physiological preconditions and usually happens during sleeping without any warning signs, such as crying, struggling or suffering. Therefore, an effective respiratory monitoring system may be a good way for early warning to reduce SIDS risk.

Infant monitoring systems, such as cardiopulmonary monitoring, vision monitoring, and oxygen consumption monitoring and multi-purpose monitoring are invasive. Such systems make the infant and the parents uncomfortable and are not as effective due to the unrecognizable signs of SIDS.

Additionally, any form of nitrogen oxide ($NO_X$) at levels greater than 1 ppm can cause serious damages to human respiration and lung tissue. The small molecules can penetrate deeply into the sensitive parts of lungs causing or worsening respiratory diseases such as emphysema and bronchitis or aggravate existing heart disease. So monitoring $NO_2$ plays an important role making working environments safer.

SUMMARY OF THE INVENTION

Provided herein are systems, methods and compositions for a wireless sensor system.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

The invention is a new method and system using sensors to non-invasively monitor external stimuli. By monitoring the outputs of sensors, detection of respiration can be monitored. The output data can be used to activate an alarm or logged for further diagnoses. With Radio Frequency Identification ("RFID") integration, the system can be used to monitor a large number of inputs.

BRIEF DESCRIPTION OF THE DRAWINGS

FIG. 15A is both in vertical polarization; FIG. 15B is one in vertical and one in horizontal polarizations; FIG. 15C is both horizontal polarization; FIG. 15D the antennae are in cross-polarizations.

DETAILED DESCRIPTION OF THE INVENTION

Figure 1A:
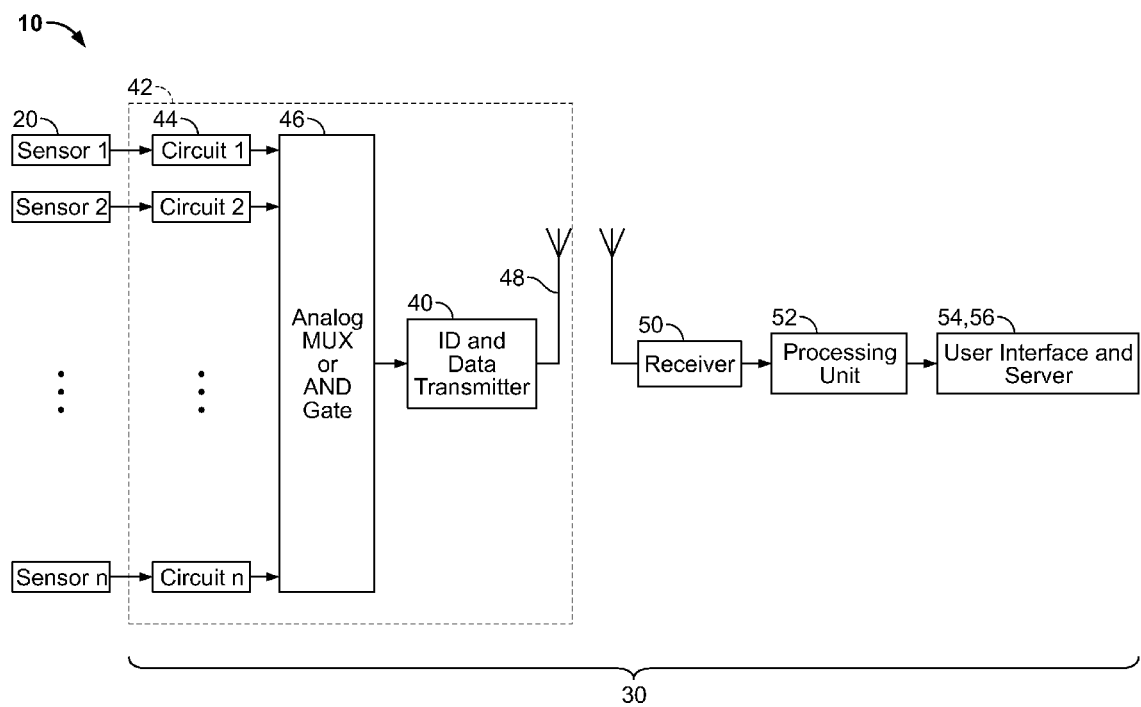
FIG. 1A is a schematic of the wireless sensor system.

The invention comprises a wireless sensor system 10, as shown in FIG. 1A. The wireless sensor system 10 comprises at least one sensor 20 and an active Radio Frequency Identification ("RFID") system 30. RFID is an automatic identification method, relying on storing and remotely retrieving data using devices called RFID tags or transponders. Electromagnetic or electrostatic coupling in the Radiofrequency ("RF") portion of the electromagnetic spectrum is used to transmit signals. The RFID system 30 comprises a transmitter 40 and a receiver 50. The transmitter 40 is otherwise known as a RFID tag and the receiver 50 is known as a reader. The transmitter 40 includes either a passive RFID transmitter tag or an active RFID transmitter tag. The passive RFID transmitter tag does not contain a battery and the power is supplied by the receiver 50. When radio waves from the receiver are encountered by a passive RFID transmitter tag, the coiled antenna within the passive RFID transmitter tag forms a magnetic field. The passive RFID transmitter tag draws power from the magnetic field by induction, which energizes the sensor circuits in the passive RFID transmitter tag. The passive RFID transmitter tag then sends the information encoded in the passive RFID transmitter tag's memory.

An active RFID transmitter tag includes an internal power source, which is used to power the integrated circuits and broadcast the signal to the receiver. An active RFID transmitter tag is for sensors with high power consumption, while the passive RID tag transmitter is for sensors with lower power consumption. Passive RFID transmitter tags are powered by energy in the receiver's signal for any on-chip computation and for communication back to the receiver. The passive RFID system can use either Near Field (Inductive Coupling) or Far Field (Backscatter Reflection) method.

The sensor 20 can comprise a gas sensor, patch-type sensors, blood pressure sensors, pulse sensor, heart rate sensors, and clamp-type sensors, such as optical $pO_2$ sensors and glucose sensors. With the RFID system approach, each type of sensor includes an identification ("ID") signal to be sent out to correlate a sensing data signal and an alarm signal with the ID signal. The sensing data signal and the ID signal can be pulled periodically for monitoring and calibration. The stored vital sign data can help to identify or diagnose any potential problems at the sensor's location.

As shown in FIG. 1A, the transmitter 40 comprises a processing circuit board 42 ("PCB"). If the RFID system is an active system, a battery (not shown) is used as the power supply for the PCB. The processing circuit board 42 comprises at least one sensor circuit 44, a multiplexer 46, and a wireless transmitter 48. The processing circuit board 42 is connected to the sensors 20 through the sensor circuit 44. The sensor circuit 44 includes a two-stage amplifier and a comparator. The first stage is for buffering and is followed the second stage, which is a differential amplifier. The comparator is implemented after the two stage amplifier. The comparator is a device which compares two voltages or currents and switches its output to indicate which is larger. The comparator sets a specific threshold for each sensor 20. After the comparator, the sensor circuit 44 outputs to the multiplexer 46. The multiplexer 46 selects one of many analog or digital data sources and outputs that source into a single channel. The multiplexer 46 multiplexes the signals from the sensor circuit 44 in the time domain. Time-Division Multiplexing ("TDM") is a type of digital or analog multiplexing in which two or more signals or bit streams are transferred apparently simultaneously as sub-channels in one communication channel, but physically are taking turns on the channel. Alternatively, the multiplexer 46 can be an AND gate, depending on the application of the wireless sensor system 10. The AND gate is a digital logic gate that implements logical conjunction to give a high output only if both the inputs to the AND gate are high and if neither or only one input to the AND gate is high, a low output results. The AND gate provides the functionality of an alarm signal to the wireless transmitter 48.

For simple monitoring purposes, the alarm signal will be sent out if the outputs from the sensors are lower than the threshold. The wireless transmitter 48 is for transmitting and receiving data from the receiver 50. With the RFID approach, an identification ("ID") signal is sent out to correlate a sensing signal and alarm signals with the ID signal. The ID signal is sent via the wireless transmitter 48 out along with the alarm signal if the outputs from the sensors 20 are lower than the specified threshold. The sensing signals are multiplexed and transmitted with the ID signal for diagnosis purposes. The threshold is adjustable for different environmental conditions for sending the alarm signal.

As shown in FIG. 1A, the receiver 50 is coupled to a processing unit 52 and a user interface 54 and server 56. The receiver 50 separates the signals by a demultiplexer for multi-modality monitoring. A demultiplexer is a device taking a single input that selects one of many data-output-lines and connects the single input to the selected output line. At the receiver side, an alarm will be triggered as soon as an alarm signal is sent by the identified transmitter 48 while the server 56 starts to record the data. Alternatively, the server may be a memory card to store data.

Figure 1B:
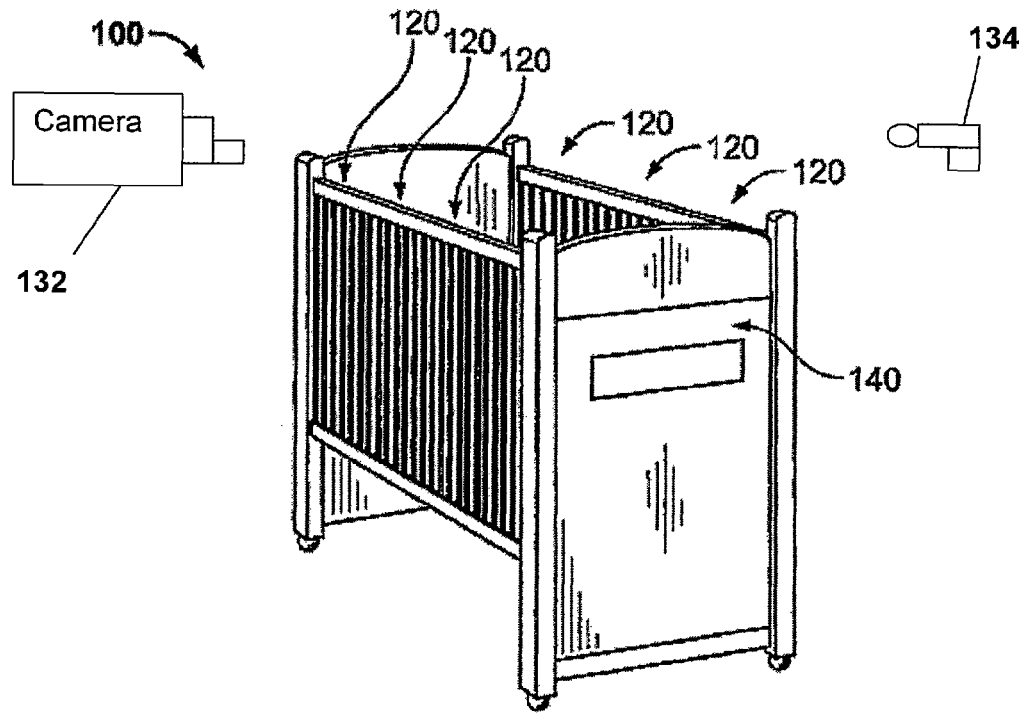
FIG. 1B is one embodiment of the invention including a crib design with sensors connected to a processing circuit board.
Figure 2:
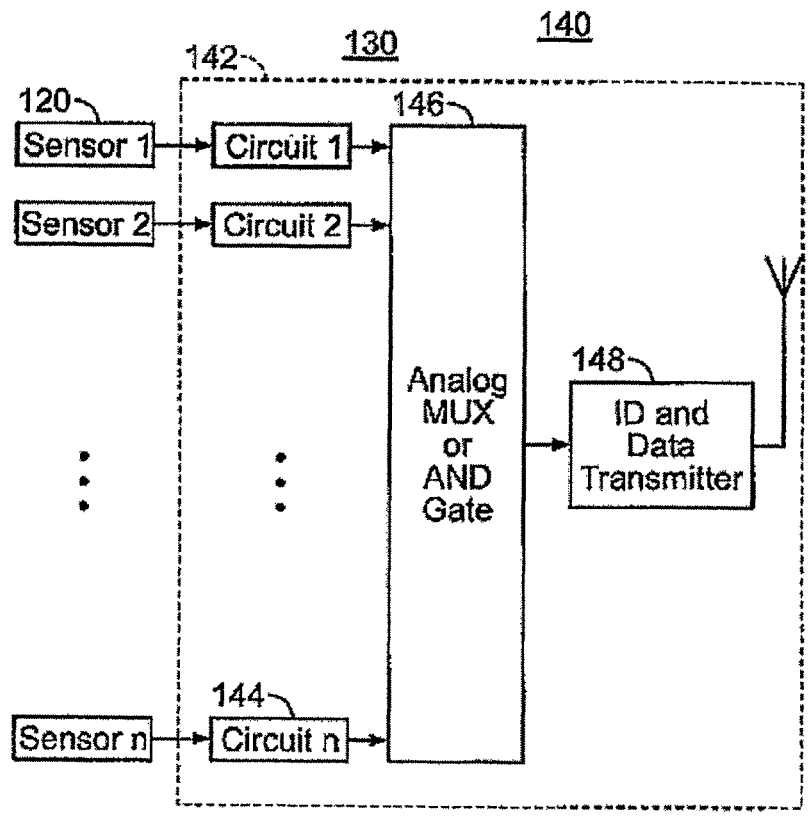
FIG. 2 is a block diagram of the transmitter.
Figure 3:
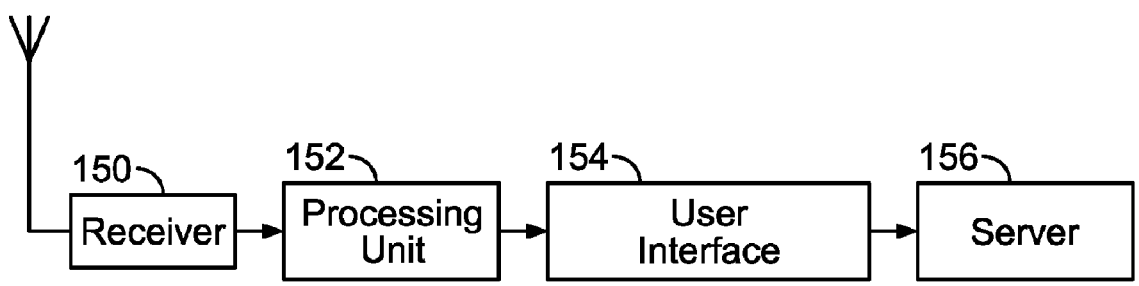
FIG. 3 is a block diagram of the receiver.

In one embodiment of the invention, the wireless sensor system 10 is an infant monitoring system 100, as shown in FIG. 1B. The infant monitoring system 100 comprises at least one sensor 120 and an RFID system 130, as shown in FIGS. 2 and 3. The sensor 120 can comprise a gas sensor, patch-type sensors, blood pressure sensors, pulse sensors, heart rate sensors, and clamp-type sensors, such as optical $pO_2$ sensors and glucose sensors. The infant monitoring system 100 can be used for infants at home, in a hospital nursery room, or in a daycare setting. The RFID system 130 comprises a transmitter 140 and a receiver 150, and can be coupled with a camera 132 and a microphone 134. The transmitter 140 is otherwise known as a tag, in an RFID system. The receiver 150 is otherwise known as the reader, in an RFID system. The RFID system may either be active or passive.

As shown in FIG. 2, the transmitter 140 comprises a processing circuit board 142. If the RFID system is an active system, a battery (not shown) is used as the power supply for the PCB. The processing circuit board 142 comprises at least one sensor circuit 144, a multiplexer 146, and a wireless transmitter 148. The processing circuit board 142 is connected to the sensors 120 through the sensor circuit 144. The sensor circuit 144 includes a two-stage amplifier and a comparator. The first stage is for buffering and is followed the second stage, which is a differential amplifier. The comparator for each sensor 120 is implemented after the two stage amplifier and then the sensor circuit 144 outputs to the multiplexer 146. The multiplexer 146 multiplexes the signals from the sensor circuit 144 in the time domain. Alternatively, the multiplexer 146 can be an AND gate, depending on the application of the infant monitoring system 100. The AND gate provides the functionality of an alarm signal to the wireless transmitter 148. The wireless transmitter 148 is for transmitting and receiving data. With the RFID approach, an ID signal is sent out to correlate a sensing signal and alarm signals with the ID signal. The ID signal is sent via the wireless transmitter 148 out along with the alarm signal if the outputs from the sensors 120 are lower than a specified threshold set by the comparator. The sensing signals are multiplexed and transmitted with the ID signal for diagnosis purposes. The threshold is adjustable for different environmental conditions for sending the alarm signal.

In one embodiment of the invention, the infant monitoring system 100 includes the processing circuit board 142 placed outside the crib to process the data, as shown in FIG. 1B. The module is away from the infant to ease parents' concern of electromagnetic waves from the wireless module. In another embodiment of the invention, the infant monitoring system 100 comprises a plurality of $CO_2$ sensors placed around the crib mounted on the inside of the bars to provide sufficient information of the concentration of gases. Infants may take various sleeping positions and the exhaled air may spread in many directions due to air circulation. A drastic variation of $CO_2$ concentration will produce an abrupt change in sensor outputs and the processor will be activated to send out an alarm signal. With the RFID approach, an identification ID signal of the infant will be sent out to correlate the sensing/alarm signals with the ID, which will significantly reduce the labor costs and time. The sensor data and ID can be pulled periodically for monitoring and calibration. The stored vital sign data can help doctors to identify or diagnose any potential health problems in infants. In another embodiment of the invention, commercial baby monitors, such as a webcam or a microphone, can be also connected to the multiplexer. For some infants who have already suffered from respiratory inborn disorders, the $CO_2$ concentration in the exhaled air is examined regularly and frequently.

As shown in FIG. 3, the receiver 150 is coupled to a processing unit 152 and a user interface 154 and server 156. The receiver 150 separates the signals by a demultiplexer for multi-modality monitoring. A demultiplexer is a device taking a single input that selects one of many data-output-lines and connects the single input to the selected output line. At the receiver side, an alarm will be triggered as soon as an alarm signal is sent by the identified transmitter 148 while the server 156 starts to record the data. Alternatively, the server may be a memory card to store data.

Gas Sensors

In one embodiment of the invention, the sensor 120 comprises a gas sensor 122. The sensor 122 may be chosen according to sensitivity, selectivity and humidity dependence. In one embodiment, the sensor is a metal-oxide based sensor. Alternatively, the sensor 122 can be an electrochemical sensor, infrared based sensor, or a nanosensor.

Figure 4A:
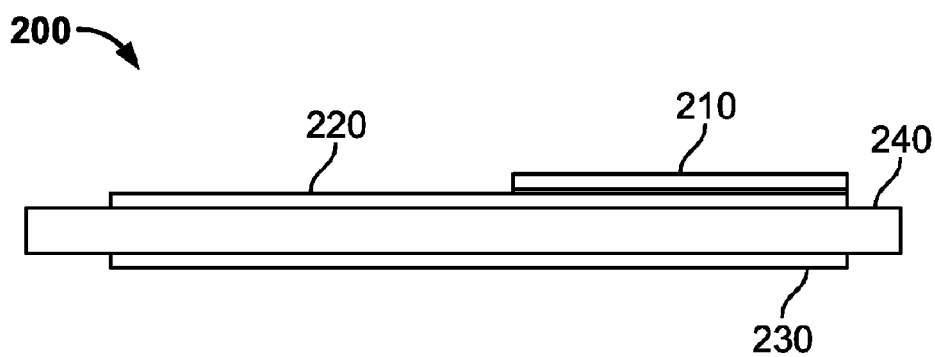
FIG. 4A is a side view of a metal-oxide sensor.
Figure 4B:
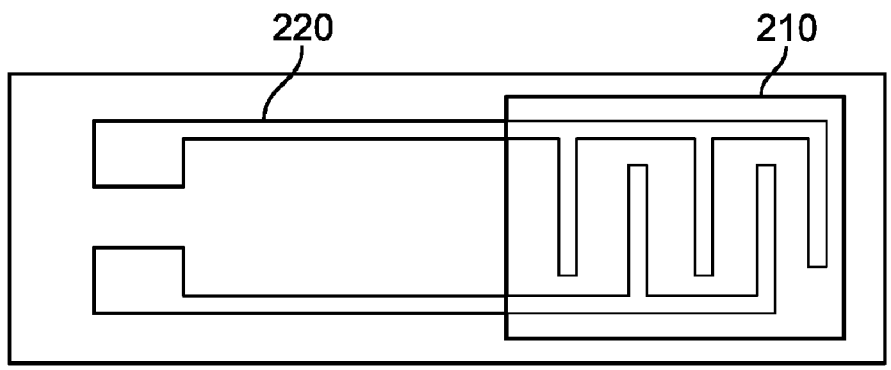
FIG. 4B is a top view of the metal-oxide sensor.
Figure 4C:
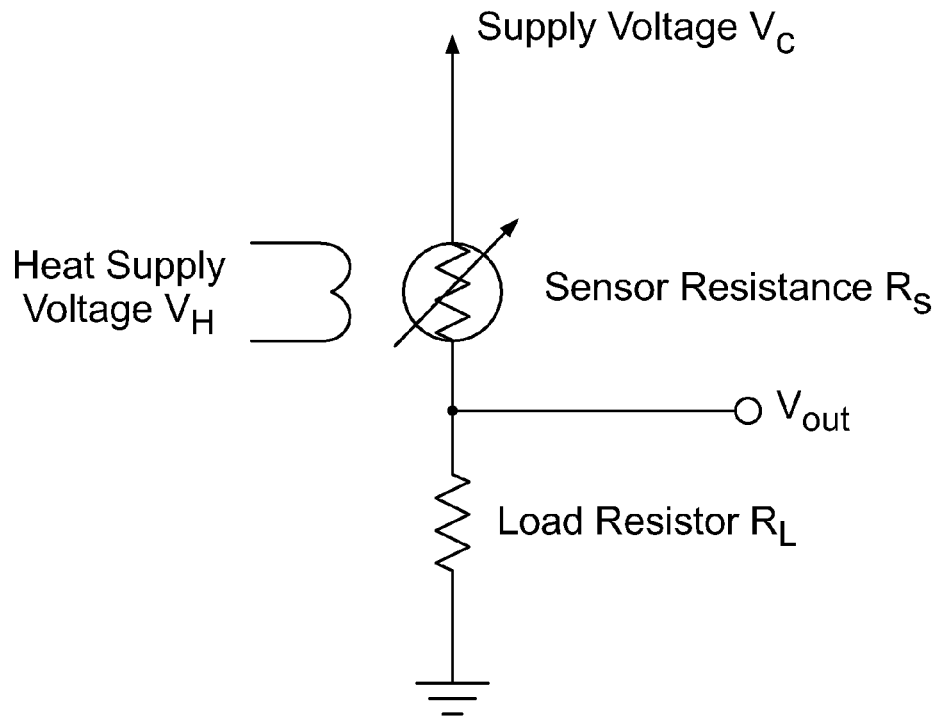
FIG. 4C is a schematic of the circuit used in metal-oxide sensors.

An exemplary metal-oxide sensor 200 is shown in FIG. 4A. Generally, the concept of metal-oxide sensors 200 comprises a sensing material 210, at least one electrode 220, and a heating element 230. The sensing material 210 reacts with the target gas molecules to induce chemical potential changes. In one embodiment of the invention, the sensing material can include tin dioxide $SnO_2$, tungsten oxide $WO_3$, or $In_2O_3$. The electrodes 220 connect to the sensing material 210 to form a closed-loop circuit. The heating element 230 is connected to a substrate 240 that is connected to the electrodes 220. The heating element 230 is used to regulate the sensor 200 temperature, since metal-oxides exhibit different gas response characteristics at different temperatures. In one embodiment of the invention, the metal-oxide sensor 200 has four electrical connections 220, as shown in FIG. 4B. Two connections are used to measure the resistance of the sensing material 210 while the other two to provide power to the resistive heater 230. The resistance changes are typically measured using a simple voltage divider as shown in FIG. 4C. The circuit requires two voltage supplies: one for the heater ($V_H$) and one for the sensor ($V_C$). $V_C$ is applied for measuring the output voltage ($V_{out}$) across a load resistor ($R_L$) and the sensor resistance ($R_S$) is calculated as equation (1):

$$R_s = \frac{V_C - V_{out}}{V_{out}} \times R_L \quad (1)$$

When a metal oxide crystal such as $SnO_2$ is heated at a certain high temperature in air, gas molecules is adsorbed on the crystal surface with a negative charge. Then donor electrons in the crystal surface are transferred to the adsorbed oxygen, resulting in leaving positive charges in a space charge layer. Thus, surface potential is formed to serve as a potential barrier against electron flow. Inside the metal-oxide sensor, electric current flows through the conjunction parts (grain boundary) of $SnO_2$ micro crystals. At grain boundaries, adsorbed oxygen forms a potential barrier which prevents carriers from moving freely. The electrical resistance of the metal oxide sensor 200 is attributed to this potential barrier.

Metal-oxide sensors 200 or solid-state sensors detect a wide variety of gases, and can be used in many different applications. The metal-oxide sensor's 200 life expectancy theoretically can last 10 years or more in clean applications. In one embodiment of the invention, the metal-oxide sensors 200 can include a charcoal filter to eliminate the affect of interference gases. The metal-oxide sensor 200 is able to detect both low levels of gases, as well as high combustible levels. The metal-oxide sensor 200 is capable of detecting lower ranges of gases at toxic concentrations while simultaneously, the combustible range for explosive concentrations of gases.

There is variety of available Commercial Metal-Oxide sensors in the market. All gas sensors from Figaro Inc. are metal-oxide base sensors including oxygen, carbon monoxide, carbon dioxide and many others while products from AppliedSensor, Inc. are based on the metal-oxide-semiconductor principle. In general, metal-oxide sensors are compact, inexpensive and have long lifetimes.

Other Gas Sensors

Other sensors include electrochemical, infrared, or nanosensors. Electrochemical sensors include the basic components of a sensing electrode, a counter electrode and a reference electrode. These electrodes are enclosed in the sensor housing in contact with a liquid electrolyte. The sensing electrode is on the inner face of a hydrophobic membrane that is porous to gas, but impermeable to the electrolyte. The gas diffuses into the sensor and through the membrane to the sensing electrode. When the gas reaches the sensing electrode, an electrochemical reaction occurs; either an oxidation or reduction depending on the type of gas. For example, carbon monoxide may be oxidized to carbon dioxide, or oxygen may be reduced to water. An oxidation reaction results in the flow of electrons from the working electrode to the counter electrode through the external circuit; and conversely a reduction reaction results in flow of electrons from the counter electrode to the sensing electrode. This flow of electrons constitutes an electric current, which is proportional to the gas concentration. The electronics in the instrument detects and amplifies the current and scales the output according to the calibration. The instrument then displays the gas concentration in, for example, parts per million (PPM) for toxic gas sensors and percent volume for oxygen sensors. Electrochemical sensors typically last only 6 months to 2 years.

Infrared sensors include an infrared source, a light tube, an interference (wavelength) filter, and an infrared detector. The gas diffuses into the light tube and the electronics measures the absorption of the characteristic wavelength of light. NDIR sensors are most often used for measuring carbon dioxide. The best of these have sensitivities of 20-50 PPM. Most are used for carbon dioxide, because no other sensing method works reliably for this gas. New developments include using Micro-Electro-Mechanical Systems ("MEMS") to bring down the costs of this sensor and to create smaller devices.

Nanosensors can include a variety of sensors with nanotechnology implemented as the sensing material. Alternatively, the metal-oxide sensor can comprise nanoparticles to maximize the surface area of the sensing element to provide for greater surface reactions with gases. Alternatively, the metal-oxide sensor can comprise a gated metal oxide sensor (Applied Nanotech). Alternatively, the sensor is a carbon nanotube field-effect transistors or multi-wall carbon nanotubes for gas sensing as in "Miniaturized gas ionization sensors using carbon nanotubes", Nature, 424, 171 (2003), herein incorporated by reference.

$CO_2$ Sensor

Human's exhaled air roughly consists of 79.5% nitrogen ($N_2$), 16.5% oxygen ($O_2$) and 4% $CO_2$. The $CO_2$ is then diffused quickly to a much lower concentration between 2000 ppm and 5000 ppm in the air. Therefore, the working range of the $CO_2$ sensor has to cover the range from 2000 to 5000 ppm of $CO_2$. The exhaled air has a saturated humidity, even after diffusion, the relative humidity ("RH") of the air composition is still high. This might introduce errors in the sensor performance, requiring us to design the system to work in a wide range of humidity. Furthermore, a short response time sensor is needed for real time monitoring purposes.

There are commercial off-the-shelf $CO_2$ sensors in the market with various sensing principles, such as electrochemical based, infrared based and metal-oxide based sensors. Electrochemical based sensors give the best performance but the short lifetime prohibits the use. Infrared-based sensors are sensitive but bulky in size and more costly. Metal-oxide based $CO_2$ sensors are low-cost and long term. Metal-oxide sensors are humidity and temperature dependent; however, testing and calibration experiments adjust the humidity and temperature dependence of the metal-oxide sensors, which will be described in later sections.

RFID Transmission

The infant monitoring system 100 can be used for one infant at home or a large number of infants in the hospital nursery room. For home uses with one infant, an RFID system is optional. The transmitter 140 will send the alarm signal and/or the $CO_2$ sensor data to a recording server to warn the parents. The sensor data can also be locally logged with a memory card. In one embodiment of the invention, the receiver 150 for monitoring purposes should be compact and mobile for the convenience to caregivers.

Figure 5:
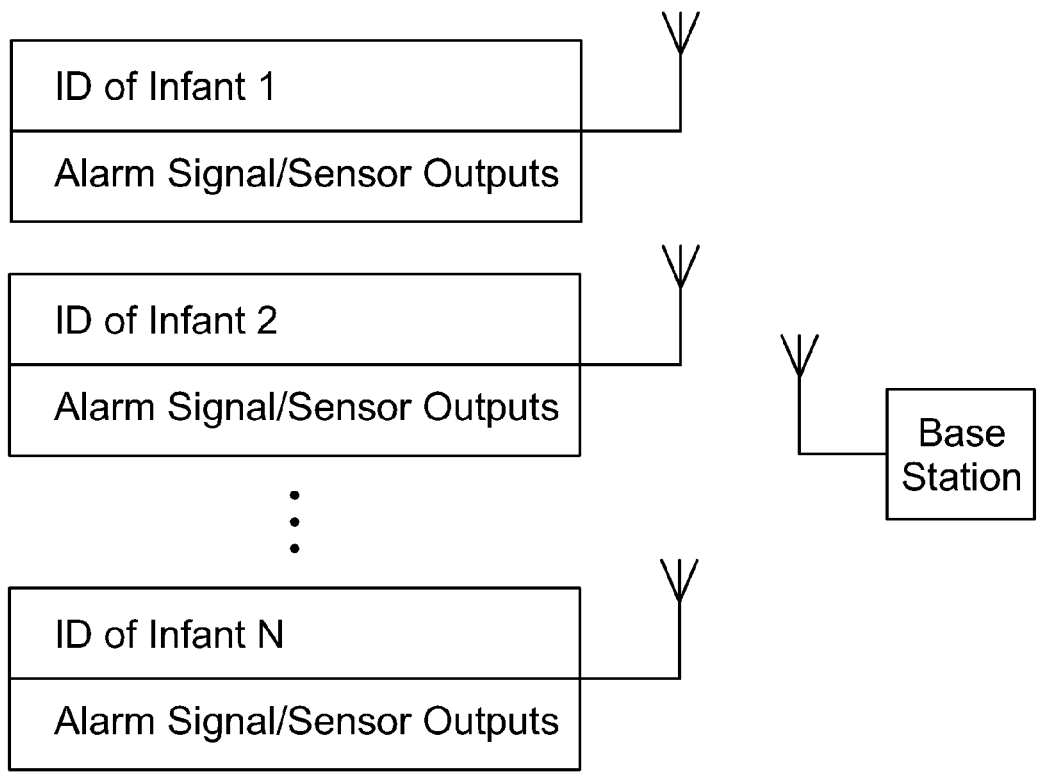
FIG. 5 is a block diagram of the system used in a hospital nursery room.

In one embodiment of the invention, the infant monitoring system 100 with integration of RFID is needed for a hospital nursery room full of infants to quickly identify individuals. A block diagram of the system architecture is shown in FIG. 5, with separate sensors with ID signals for each infant and associated RFID systems communicating with the base station. The passive RFID tags can be utilized to identify the infant. If the power consumption for the sensor is much higher than the transmitted power of a passive RFID system, then a typical active RFID system can provide sufficient power to the sensor. An active RFID system can transmit a power of 1 mW, while the carbon dioxide sensor power consumption is around 250 mW. An active RFID approach gives a longer communication distance and operation flexibility.

To minimize reader collision for the infant monitoring system 100 in a passive RFID system Colorwave algorithm, HiQ algorithm, Pulse Protocol Algorithm, Frequency Division Multiple Access ("FDMA'), Time Division Multiple Access ("TDMA"), Code Division Multiple Access ("CDMA") and Carrier Sense Multiple Access/Collision Avoidance ("CSMA/CA") methods can be employed. Colorwave algorithm is a representative of algorithms that use a distributed system with a distributed algorithm, such that a reader network with each reader node has the smallest possible number of adjacent nodes to avoid collision. HiQ algorithm or Hierarchical Q-Learning minimize reader collisions by learning the collision patterns of the readers and by effectively assigning frequencies over time to ensure neighboring readers do not experience collisions from one another. In a Pulse Protocol Algorithm, a reader listens on the control channel for any beacon for $T_{min}$ time before communicating, and if no beacon on the control channel for $T_{min}$, starts communication on the data channel. FDMA access technology to share the radio spectrum amongst multiple users by allocating multiple users with different carrier frequencies of the radio spectrum. TDMA a channel access method for shared radio networks to allow several tags to share the same frequency channel by dividing the signal into different timeslots. CDMA is a method of multiplexing that divides up a radio channel by using different pseudo-random code sequences for each tag. CSMA/CA dictates a tag wishing to transmit has to first listen to the channel for a predetermined amount of time so as to check for any activity on the channel.

Although an active RFID system includes only one receiver, receiver/reader collision issues exist among active RFID transmitters when they are trying to send signals to the base station simultaneously. Anti-collision methods for passive RFID systems can be implemented for the active RFID system. In one embodiment of the invention, for a full active RFID monitoring system, TDMA can partition alarm transmission and recording periods efficiently if the data burst rate is sufficiently high. In another embodiment of the invention, for a simple active RFID monitoring system, the transmitter tag sends out the alarm signal along with the ID signal only when the sensor outputs give improper data values. Normally, the transmitter tag will be in a sleeping mode to save energy. CSMA/CA overcomes reader collision when two different transmitter tags transmit at the same time. Each transmitter tag includes listening functionality that can be used for the Listen Before Talk ("LBT") and the Delay Before Talk ("DBT") mechanisms. LBT dictates that a reader must listen and confirm that a particular channel is not occupied before it can use that particular channel to interrogate any transmitter tag. DBT dictates that a reader will be delayed before talking to the reader if a particular channel is occupied.

Figure 6A:
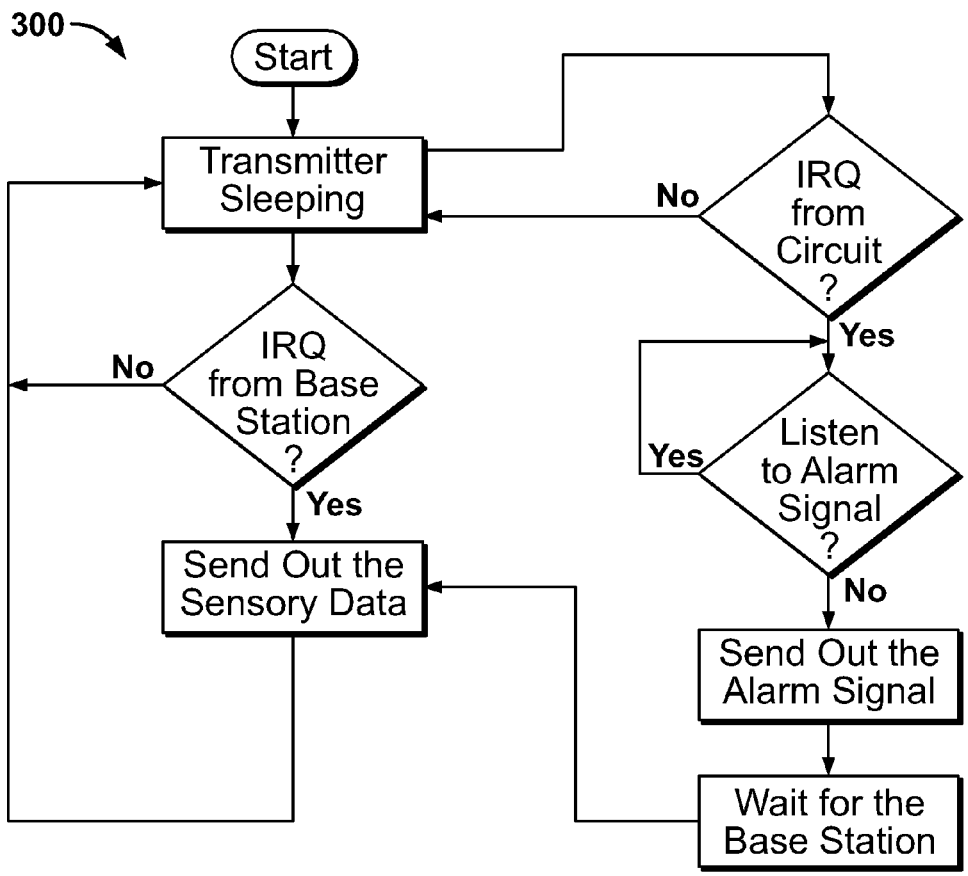
FIG. 6A is the transmitter algorithm and FIG. 6B is the base station algorithm.

In the infant monitoring system 100, each transmitter 140 is in the sleeping mode and will be waken up only when its sensor circuitry sends an alarm signal or the base station sends a request to receive sensory data, as shown as the Transmitter Algorithm 300 in FIG. 6A. The alarm signal of each sensor is the ID signal designated for the crib. Additionally, each crib will be associated with a particular set of ID signals, which is used to assign each crib with an identification label. The sensory data sent by the request of the base station is in packages containing both sensor ID and sensor signal. First, the base station will listen for any alarm signal, if there is no alarm it will transmit the request to a certain crib. The RFID listens and if the ID matches, the transmitter will be waken up and send out the sensory data signal. The base station collects the sensory data signal and records the data in a memory system. The sensory data package takes a small time slot and then the reader listens to alarm signals again. If there is no alarm, the reader pulls the second ID to request data from the second crib. This process repeats until all cribs are recorded. The caregivers have to physically reset alarms, if the reader receives them.

Figure 6B:
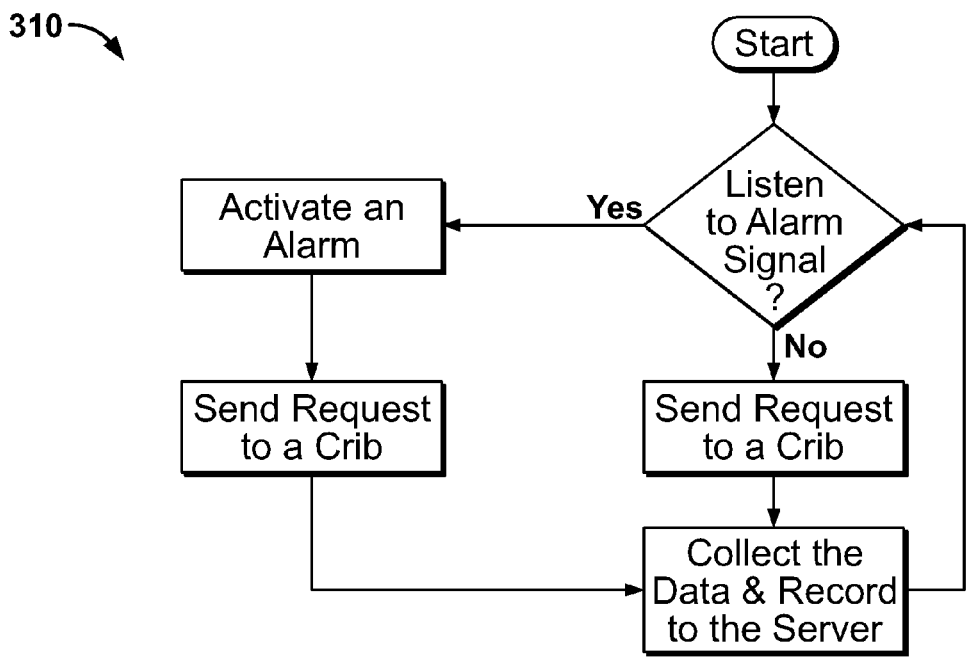

If something happens with a specific infant, the transmitter will listen first before sending to avoid collision. The alarm will be sent continuously until the next listening timeslot of the base station. If another crib is sending an alarm signal, it will wait until the medium is free. When the base station obtains an alarm signal from a crib, it will activate an alarm and send request to that crib. The base station algorithm 310 is shown in FIG. 6B. That crib will stop sending the alarm signal and send the sensory data. The data pulling order then is changed. The alarm in the base station can only be cleared by a user inputted command. To avoid collision between two transmitters as one is transmitting sensor data while the other one is transmitting alarm signal, two RF channels can be used.

EXAMPLES

The following examples are put forth so as to provide those of ordinary skill in the art with a complete disclosure and description of how the compositions, compositions, articles, devices, systems, and/or methods claimed herein are made and evaluated, and are intended to be purely exemplary and are not intended to limit the scope of compositions, compositions, articles, devices, systems, and/or methods. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 7A:
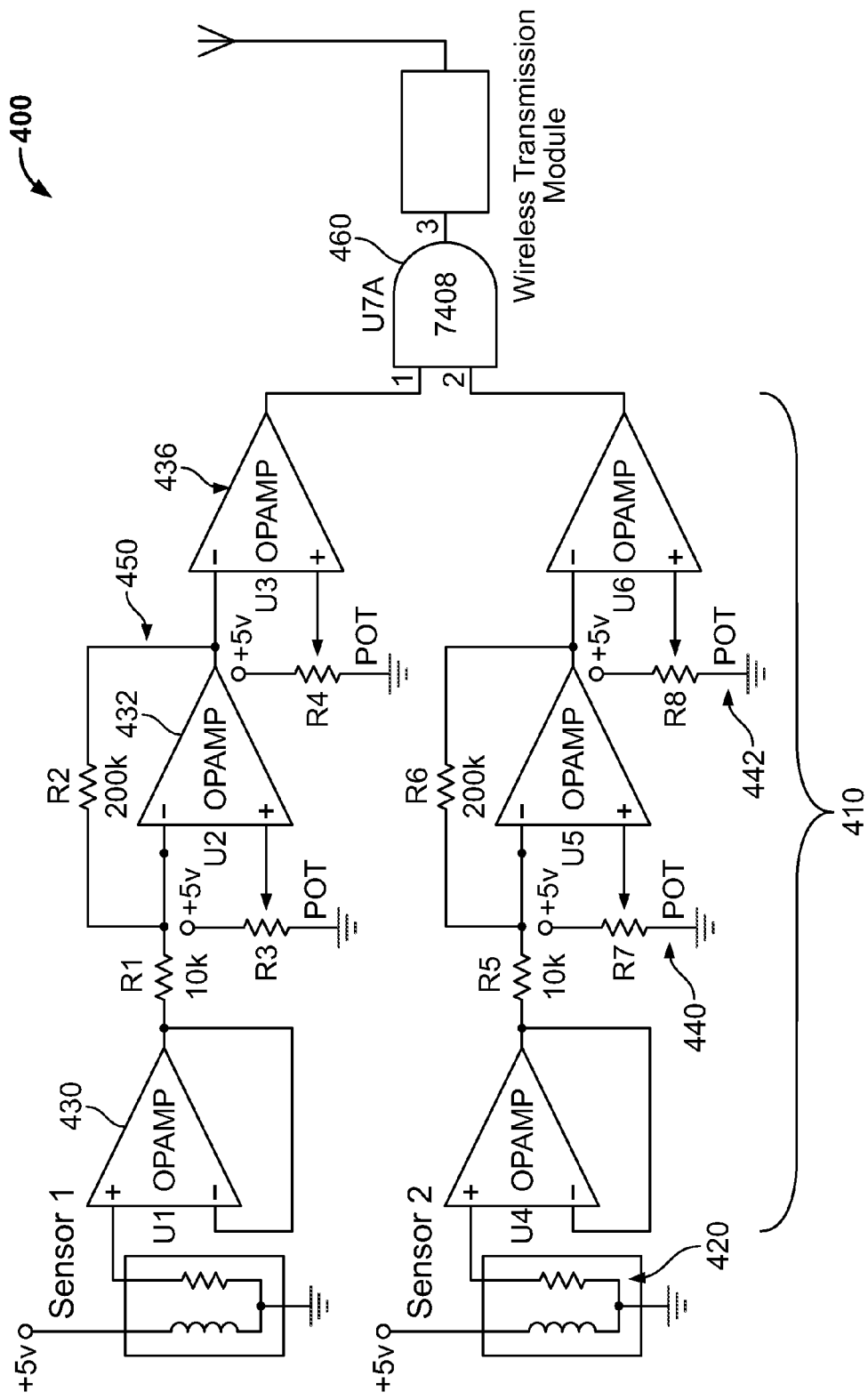
FIG. 7A is a schematic of the PCB of the transmitter and FIG. 7B is the assembled PCB of the transmitter.
Figure 7B:
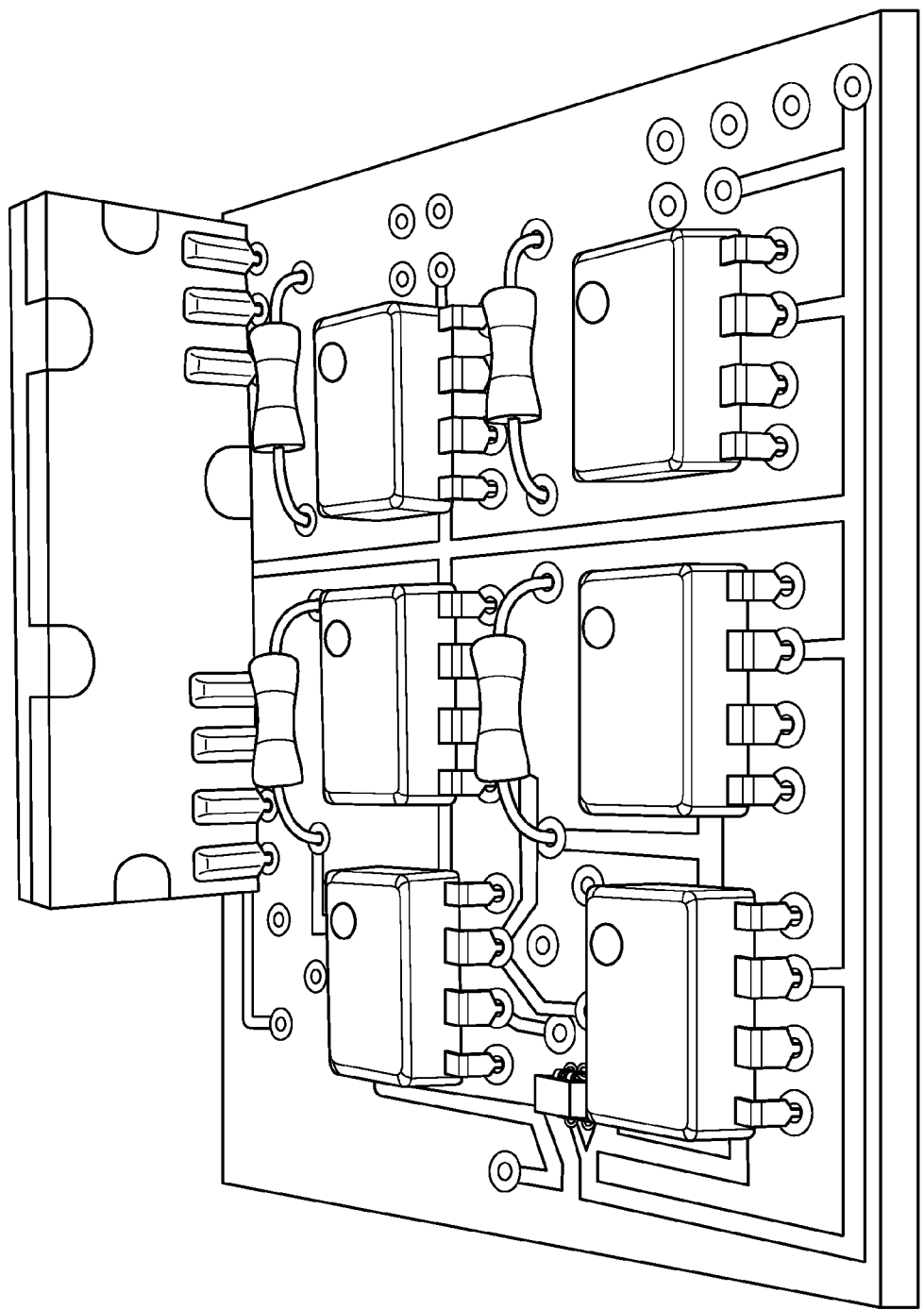

An active RFID system comprises at least two transmitter tags and at least one common receiver, as shown in FIG. 7A. In one embodiment of the invention, one transmitter tag includes a 914 MHz frequency and a second transmitter tag includes a 433 MHz frequency. The receiver talks to two transmitters at the same time. The identification signal is encoded in the operating frequency. The sensor circuits were designed and assembled with two-layer Printed Circuit Boards 400 ("PCB"). FIG. 7A shows the schematic and assembled PCB of the transmitter The PCB 400 comprises at least two sensor circuits 410 and at least two sensors 420. The sensor circuit comprises at least three Operational Amplifiers 430 ("OPAMPs") and at least two potentiometers 440. OPAMPs are a DC-coupled high-gain electronic voltage amplifier with Differential Inputs and a single output. OPAMPs such as a TI TLC271 may be used (Texas Instruments). A potentiometer is a variable resistor that can be used as a voltage divider. The first potentiometer 440 is used to create a differential voltage. The difference in voltage is then amplified by an OPAMP 432 with a gain factor of Equation (2):

$$A_V = \frac{R_2}{R_1} = \frac{200\,k\Omega}{10\,k\Omega} = 20 \qquad (2)$$

Figure 8A:
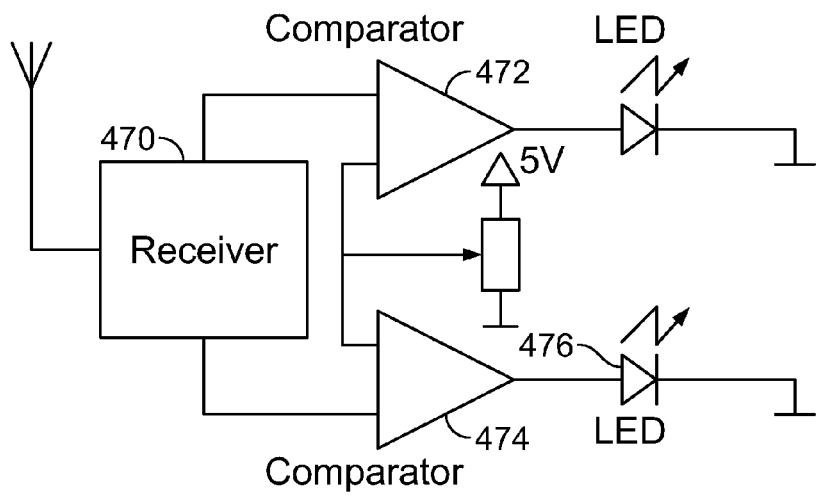
FIG. 8A is a schematic of the PCB of the receiver and FIG. 8B is the assembled PCB of the receiver.
Figure 8B:
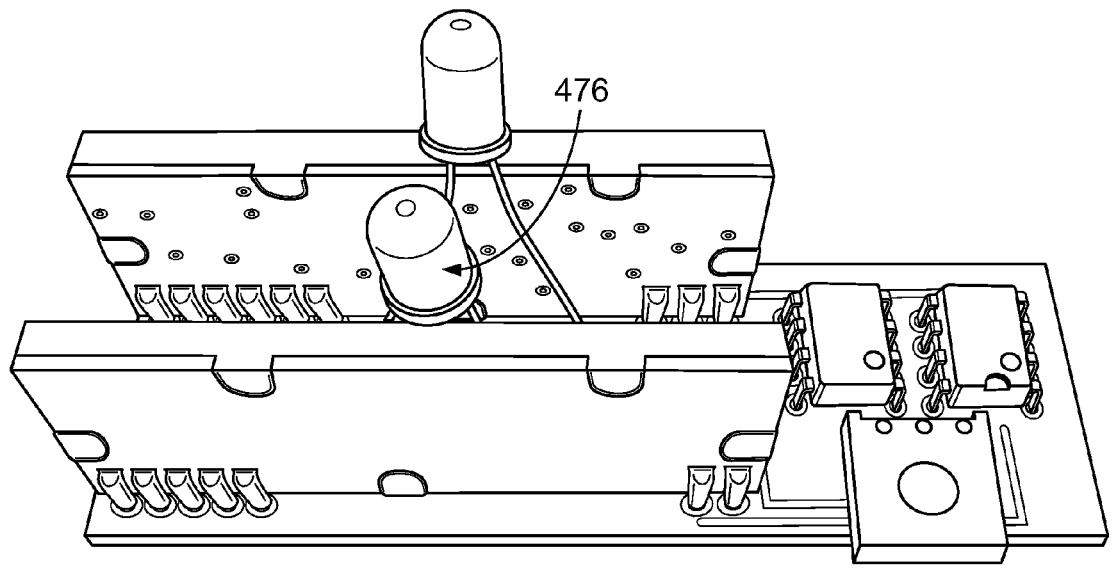

The second potentiometer 442, after the buffer 450, and the differential amplifiers, is used to set a threshold voltage. When the sensor signal is lower than the threshold voltage, the third OPAMP 436 working as a comparator will give a 5V output as the input to the AND gate. If responses from all sensors show low concentrations of $CO_2$, the output of the AND gate is set to 5V and sent to the wireless module 460. The wireless module includes one transmitter working at a first frequency and a second transmitter working at a second frequency. In one embodiment of the invention, the first frequency is different than the second frequency. In one embodiment of the invention, the first frequency is at 914 MHz (TX3A, Radiometrix) and the second frequency is at 433 MHz (TX2A, Radiometrix). The receiver 170 (RX3A, RX2A, Radiometrix) receives data from the two transmitters and processes them separately with a first and a second comparators 472, 474 using OPAMPs. When a transmitter sends an alarm signal, the output of the comparator will be 5V and turn on a Light Emitting Diode 476 ("LED") as an alarm indicator, as shown in FIG. 8A and FIG. 8B. The alarm algorithm is simplified in this approach. Designed experiments can determine how to set the thresholds in different sensors around the crib and how to process the data to trigger the alarm.

Example 2

Carbon Dioxide Sensor Tests

Figure 9:
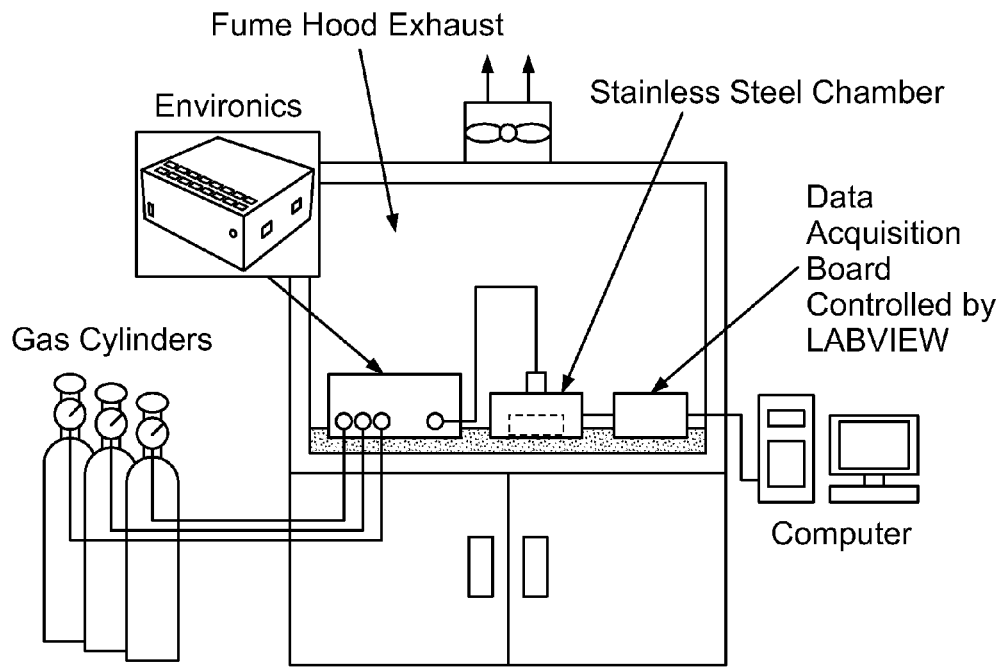
FIG. 9 is a characterization setup for gas sensors.

Gas sensor characterization depends on many environmental parameters. Figaro TGS4161 $CO_2$ sensors were characterized in various types of environmental conditions, as shown in FIG. 9. A gas mixing system (Environics Series 4000) generated concentrations of $CO_2$ in a composition with other gases such as $N_2$ and $O_2$ and with humidity control. The air flow from the gas mixing system was enclosed on the $CO_2$ sensor by a stainless steel chamber. The temperature in the infant room does not change significantly. FIG. 9 shows the configuration of the experimental setup, where all equipment was placed in a fume hood located in a class-10,000 cleanroom, except the gas cylinders and computer. The output from the $CO_2$ sensor was recorded through a data acquisition board controlled by software (LABVIEW, National Instruments).

Sensitivity Test

Figure 10:
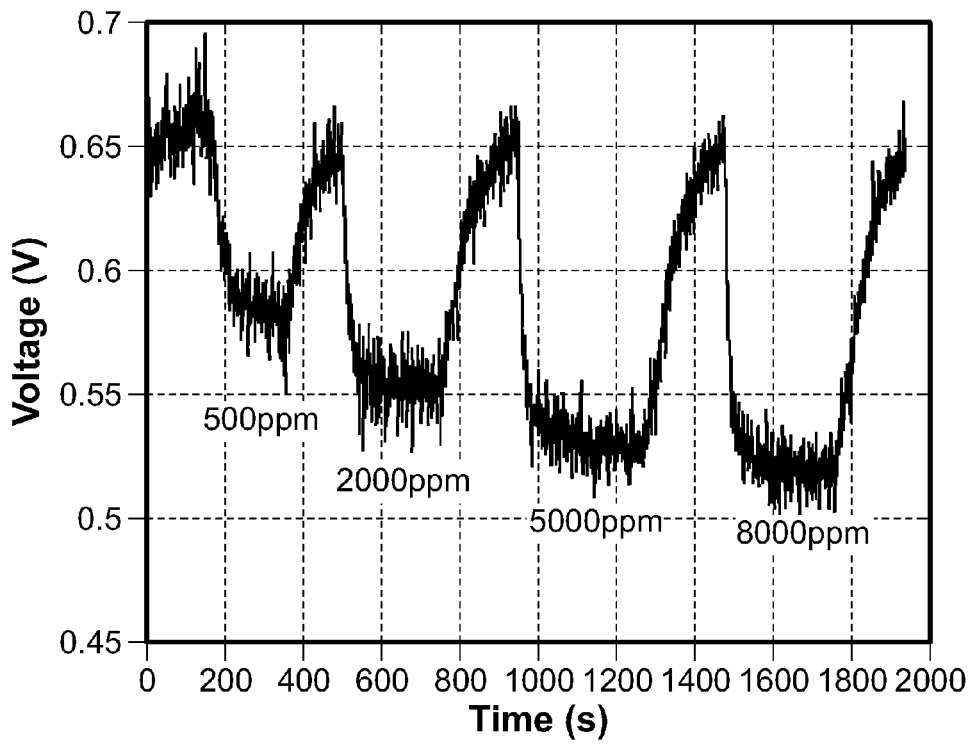
FIG. 10 is a graph of the sensitivity test results.

The $CO_2$ concentrations chosen for sensitivity tests were 500, 2000, 5000 and 8000 ppm with a gas flow rate of 1000 ccm at the room temperature (24° C.) and zero humidity. The sensitivity tests were done by first purging the chamber with 100% $N_2$ and then supplying $CO_2$ diluted in $N_2$ for measurement. FIG. 10 shows the output voltage from the sensor with various $CO_2$ concentrations.

Figure 11:
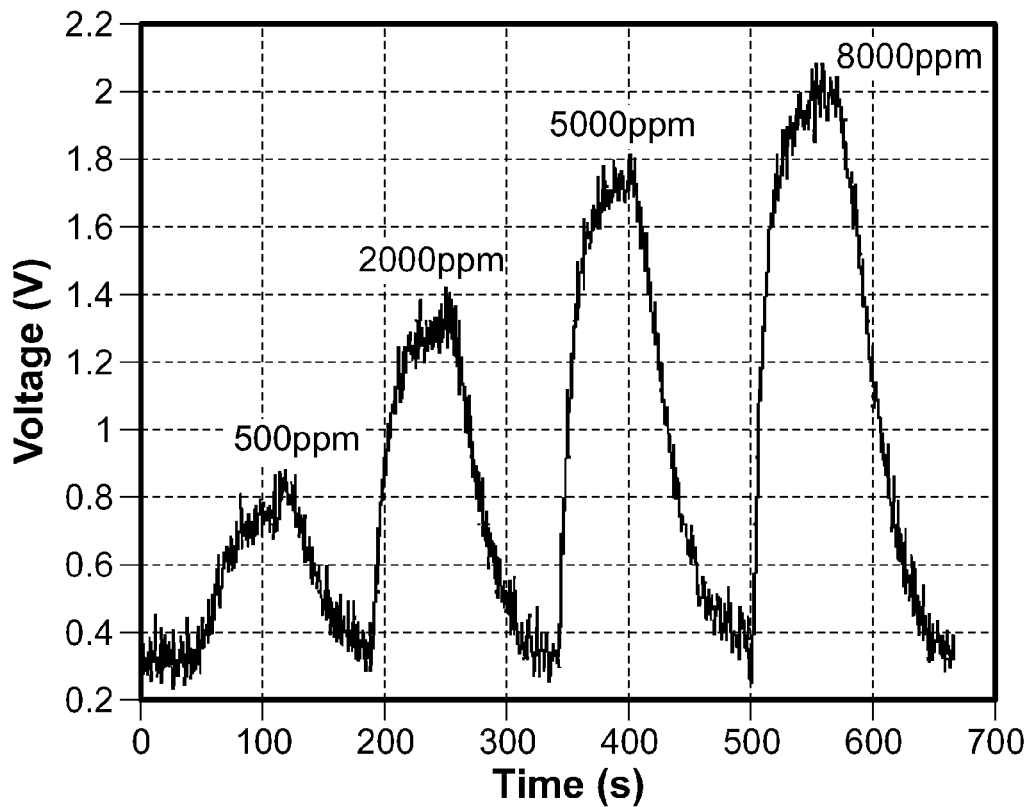
FIG. 11 is a graph of the processed sensor signals.

The differential amplifier was used to magnify the change in voltage. FIG. 11 shows the signal after two stages of amplifiers with various concentrations of $CO_2$. The sensitivity is about 0.2 mV/ppm in the range of 500-5000 ppm. The rise and fall response times are defined as the times for the output voltage to reach 90% of its final value or drop to 10% of its stable level, respectively. The respective rise and fall response times are in ranges of 5-15 s and 30-50 s for four tested concentrations. In the infant monitoring system, the fall time from 2000-5000 ppm of $CO_2$ to the ambient $CO_2$ density of 350-750 ppm is of particular importance. In FIG. 11, the fall times from 2000 and 5000 to 500 ppm of $CO_2$ are 10 and 15 seconds, respectively. The response times are too long for monitoring respiration. Alternatively, the drop rate in the first two seconds is used instead of detecting the absolute values to monitor respiratory changes from 2000 and 5000 to 500 ppm of $CO_2$.

Selectivity Test

Figure 12:
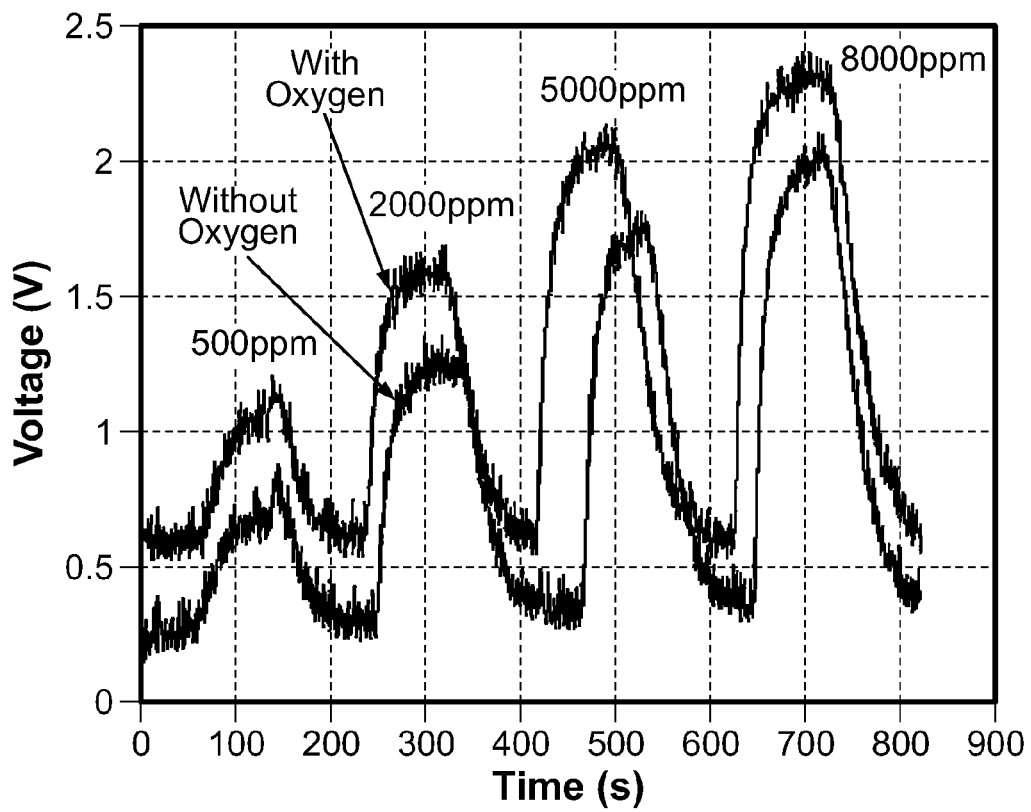
FIG. 12 is a graph of the responses of the composition with 16.5% $O_2$ and the one without $O_2$.

The sensor signal is only affected by $CO_2$, while other gases like CO and $H_2$ will have no effect (TGS4161, Figaro). The $CO_2$ sensor operated in an environment with the presence of $N_2$ and $O_2$. Therefore, the selectivity tests were carried out with a composition of $N_2$ as the balance gas, 16.5% $O_2$ and different concentrations of $CO_2$ at 40% RH. The response was then compared with the one obtained without the presence of $O_2$. FIG. 12 shows that the sensor signal with the presence of $O_2$ is about 0.25V greater than the one without $O_2$. Thus, the threshold voltage setting is adjusted accordingly.

Humidity Dependence Test

Figure 13:
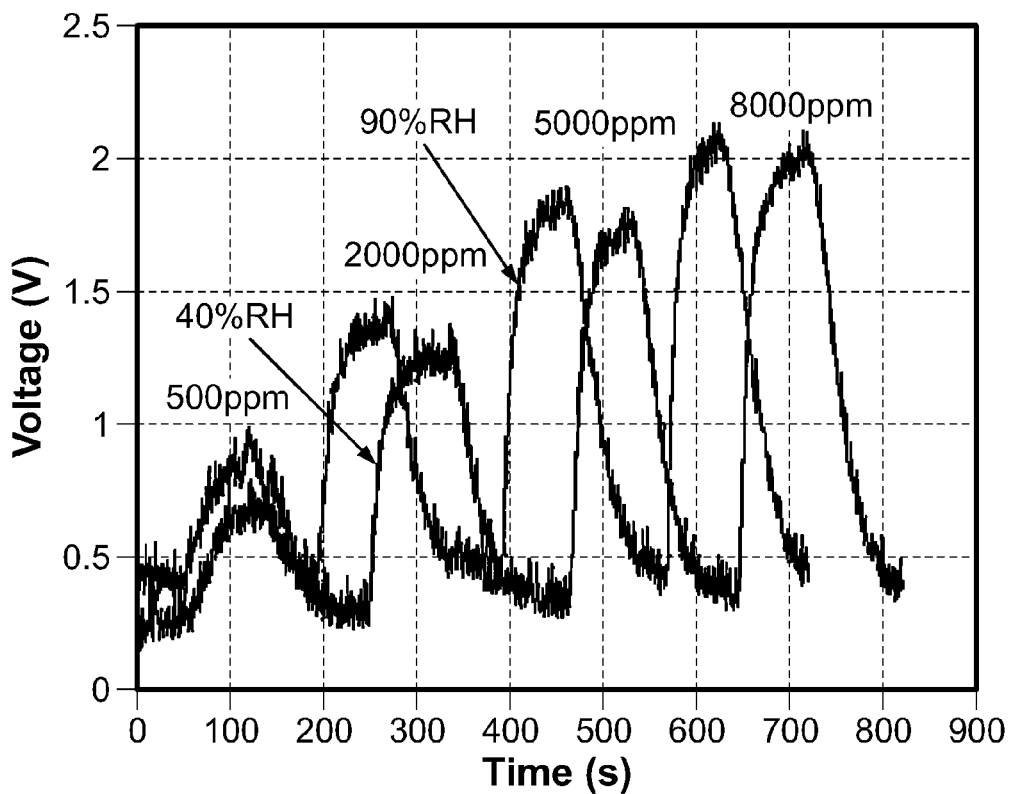
FIG. 13 is a graph of the responses at 90% RH and 40% RH.

Metal-oxide sensors usually are sensitive to humidity, because the water molecules prevent the binding of the target gas to the sensing membrane. The humidity dependency of the $CO_2$ sensor does not apply for room temperature conditions. Amplifiers can magnify the variations due to the humidity effects. Tests were conducted by first fixing the RH level in the gas mixing system, purging the chamber with 100% $N_2$ as the balance gas, and then supplying $CO_2$ with different concentrations for measurement. The process was then repeated with several levels of humidity. Results showed that with small changes in RH, the sensor signals stayed stable. Test results at 40% RH and 90% RH are shown in FIG. 13. In FIG. 13, the variations are 23%, 7%, 5% and 2% for 500 ppm, 2000 ppm, 5000 ppm and 8000 ppm of $CO_2$, respectively. Therefore, the threshold needs to be adjusted with the respective values of relative humidity.

Sensor Test with Breaths

Figure 14:
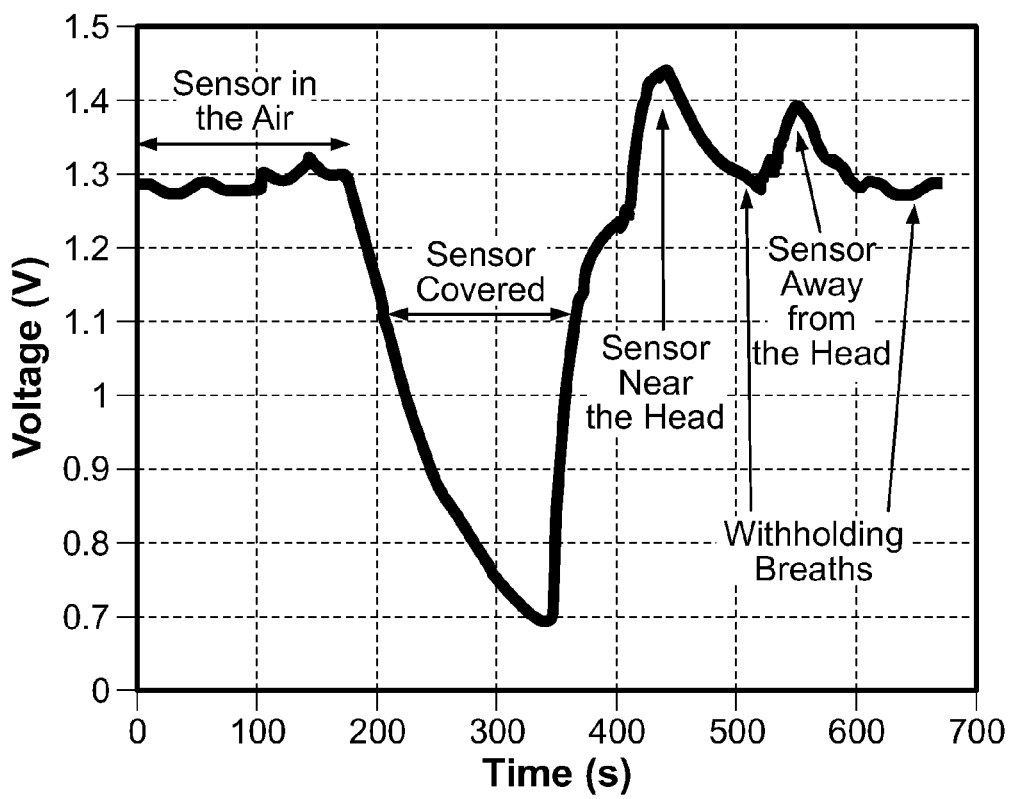
FIG. 14 is a graph of the sensor responses with different sensor locations.

Performance tests of the sensors in practical conditions by breathing near the sensor at different distances, as shown in FIG. 14. First, the sensor is in air with the presence of ambient $CO_2$ (350-750 ppm), and then the sensor is covered by a chamber with pure $N_2$, which shows a drop in voltage. Then, the chamber was removed and the sensor is tested by breathing and withholding breaths at different distances. As shown in FIG. 14, the output voltage drops when withholding breaths. When the sensor is near the head, i.e. breath is close to the sensor, the output voltage is higher than when the sensor is away from the head. The distance dependence is addressed with multiple sensors to coordinately detect the highest concentration of $CO_2$ at any given time, as in the infant monitoring system.

RF Transmission Test

Figure 15A:
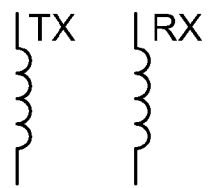
FIGS. 15A-D are different antenna polarizations.
Figure 15B:
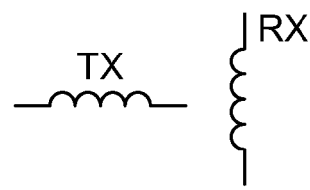
Figure 15C:
Figure 15D:
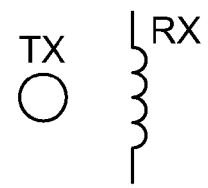

The wireless module 460 has a nominal output power of 1 mW and an in-building transmission distance of 75 m. The coil antennae tested the transmission capability with various polarizations of antenna in a narrow hallway and in different sizes of rooms as well, as shown in FIG. 15A-D. FIG. 15A is both in vertical polarization; FIG. 15B is one in vertical and one in horizontal polarizations; FIG. 15C is both horizontal polarization; FIG. 15D the antennae are in cross-polarizations. Results show that the received powers are always sufficient to correctly trigger the alarms and record the sensor signals System Test The active RFID sensor system was tested by breathing near the sensors with a distance of 50 cm for 30 seconds and then withheld our breathing for 20 seconds. Various head directions and positions were tested. The receiver 470 was placed at different distances and in another room. A few seconds after the tests started, the LED was turned on by the alarm signal. The tests were repeated with two people using two sets of sensors/transmitter, where the results were the same.

Figure 17A:
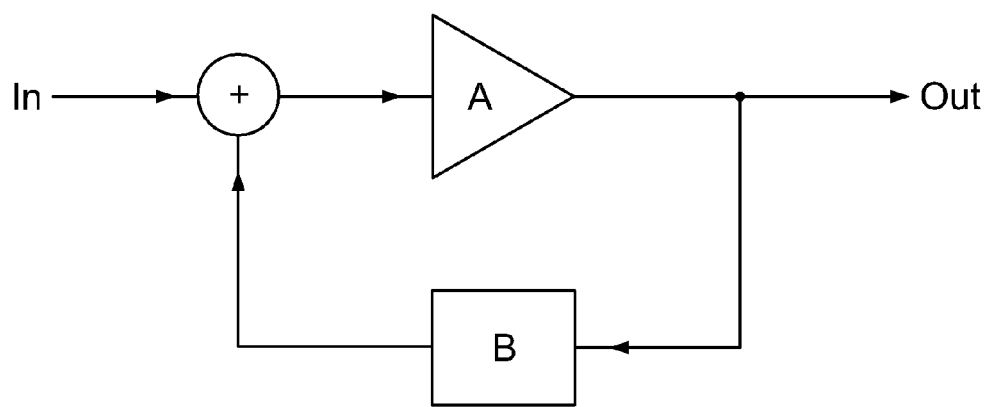
FIG. 17A is a negative feedback loop, and 17B is a block diagram of a compensation system.
Figure 17B:
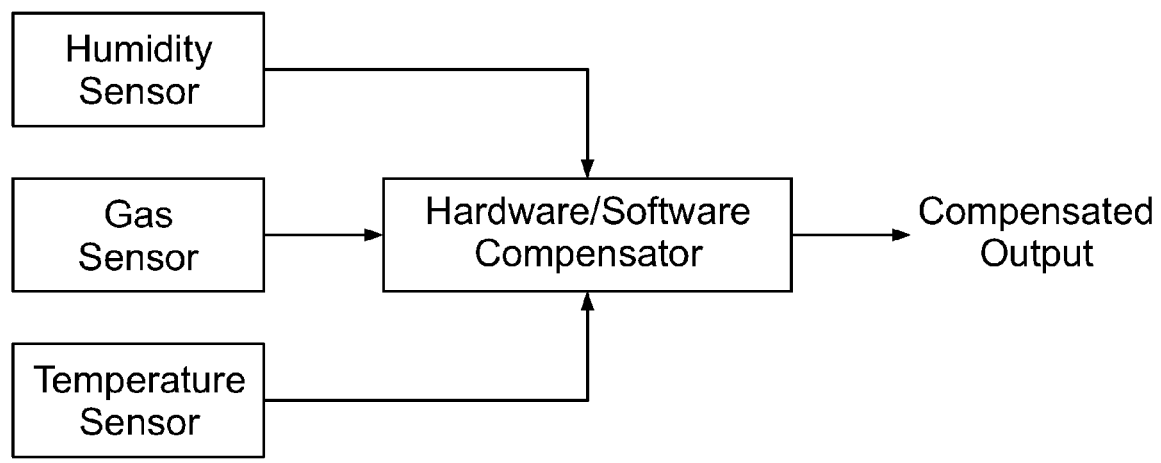

One of the critical elements is the sensor performance, especially the uniformity among devices. During the sensor tests, there was a slight variation in the outputs between two different sensors and the outputs from a certain sensor were not identically repeatable for the same concentration of gas. The output signals also change over time for the same concentration. Although those changes are relatively small, it may issue false alarms and desensitize caregivers' attention. A sensitive yet stable sensor with performance uniformity is preferred. For the humidity dependence issue, water vapor hinders the chemical reaction between the target gas and the sensing material for metal-oxide sensors. The humidity dependency of the metal-oxide sensors is resolved by adding a humidity sensor in the PCB sensor boards. The threshold voltage will be accordingly adjusted by a feedback loop. The signal is looped back to control the sensor system within itself, such as a negative feedback. Negative feedback feeds part of the system's output, inverted, into the system's input; generally with the result that humidity fluctuations are attenuated, as shown in FIG. 17A. The negative feedback is introduced to increase the stability and accuracy of a system, as in the feedback amplifier. As shown in FIG. 17B, a compensation circuit and/or software using a temperature and/or a humidity sensor integrated along with the gas sensor. The output is adjusted to accommodate humidity and temperature fluctuations, whereby the gas sensor outputs are compensated by the humidity and temperature sensor output to provide for accurate readings of the sensor output.

Relative humidity/temperature and relative humidity sensors are configured with integrated circuitry to provide on-chip signal conditioning. Absorption-based humidity sensors provide both temperature and % RH voltage outputs. On-chip signal processing ensures linear voltage output versus % RH. Relative humidity sensors should provide +5% RH accuracy and achieves 2% RH accuracy with calibration. The humidity sensors are chemically resistant and operate in ranges of −40° C. to 85° C. to accommodate harsh environments.

$NO_2$ Sensors

Any form of nitrogen oxide ($NO_X$) at levels greater than 1 ppm can cause serious damages to human respiration and lung tissue. The small molecules can penetrate deeply into the sensitive parts of lungs causing or worsening respiratory diseases such as emphysema and bronchitis or aggravate existing heart disease. $NO_2$ is also a source of acid rain, damaging buildings and polluting water sources. So monitoring $NO_2$ plays an important role making our environment safer and cleaner.

Figure 16:
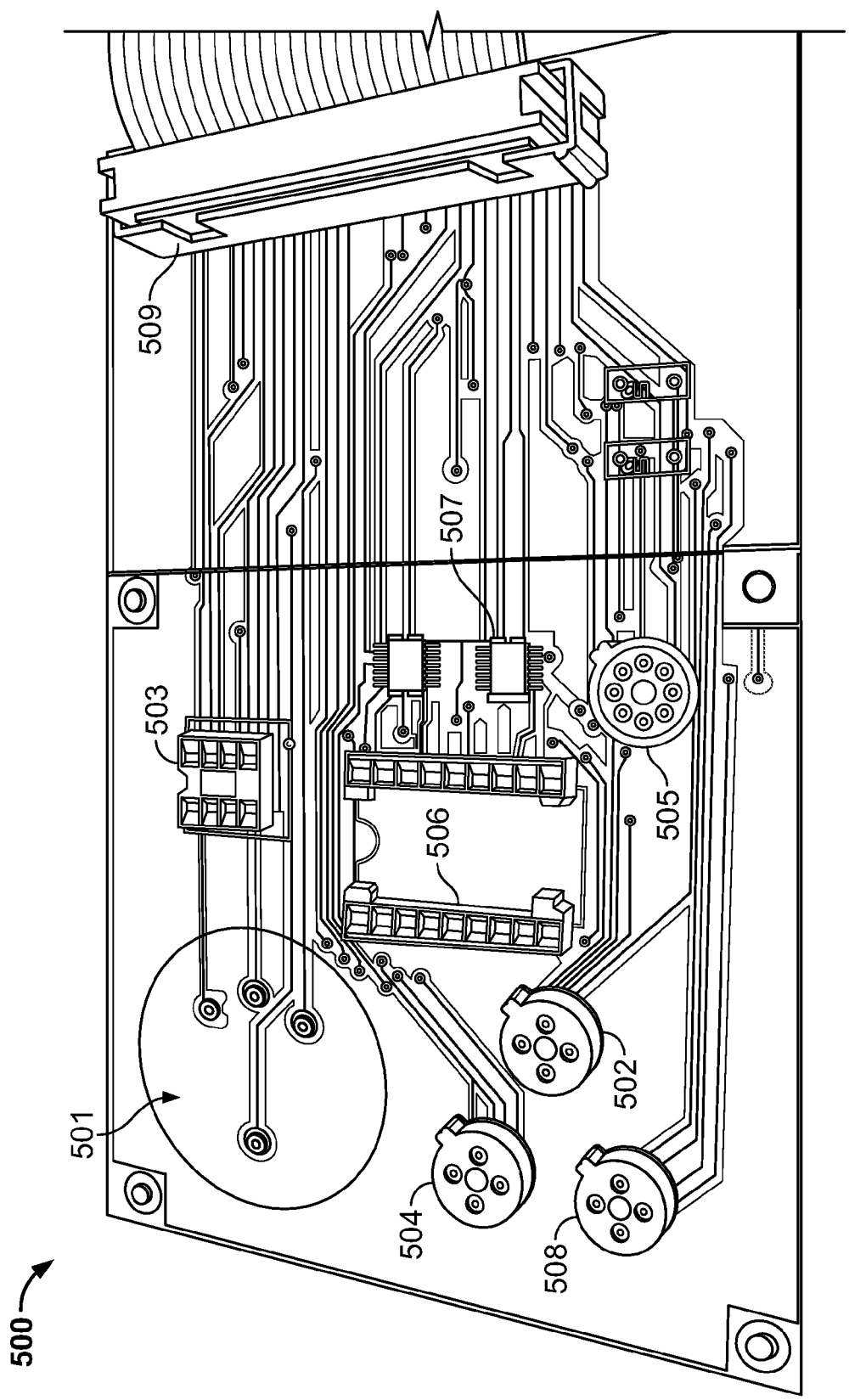
FIG. 16 is the PCB board with multiple sensors.

In one embodiment of the invention, multiple sensors can be implemented on the transmitter tag, as shown in FIG. 16. Four sensors 501, 502, 503, 504 were mounted in the sockets of a PCB board 500 as shown in FIG. 16. A combined humidity and temperature sensor 505 was integrated on the PCB board 500 to monitor the environmental conditions. One example of the combined humidity and temperature sensor 505 is from Honeywell (HIH-3602-C). An $NO_2$ sensor 506 was placed on the board 500 with two Integrated Circuits 506. The board can also include other gas sensors 508 ($CO_2$, $O_2$, CO, etc.) to monitor mixed gases during the selectivity tests. The sensors 501-504 manufacturers provided evaluation boards with the sensors. The evaluation boards are connected to the sensors through the ribbon cable 509 on the PCB board. A LabVIEW data acquisition card acquires the sensor signals for the sensors A, B, and C. A software package provided by the manufacturer was used for the sensor D. A stainless steel chamber with dimensions of 7×7×3 cm³ was used to enclose the PCB. The mixed gas was supplied through a tube at the top of the chamber.

Three metal-oxide $NO_2$ sensors were evaluated and an electrochemical $NO_2$ sensor was also evaluated as a reference inside a fume-hood in a class 10,000 clean room as indicated previously. The metal-oxide $NO_2$ sensors have a sensing range of 0.1-200 PPM, a response time of seconds, a temperature range of −40° C.-100° C., humidity range of 0-99%. The metal oxide $NO_2$ sensors can have a power consumption of 35 mW-750 mW; can have a cell life of greater than 5 years. The $NO_2$ concentrations for the sensitivity tests were 1.2, 2.0, 5.0, 8.0, and 10.0 PPM. The tests were performed both by increasing and decreasing the $NO_2$ concentration between 1.2 and 10.0 ppm The $NO_2$ concentrations chosen for the sensitivity tests were 1.2, 2.0, 5.0, 8.0, and 10.0 ppm with a gas flow rate of 1000 ccm at the room temperature (24° C.) and zero humidity. The tests were done by first purging the chamber with $N_2$ for 3 minutes and supplying diluted $NO_2$ for measurement. This procedure was repeated for various concentrations. The tests were performed both by increasing and decreasing the $NO_2$ concentration between 1.2 and 10.0 ppm.

Three metal-oxide $NO_2$ sensors were evaluated and compared to an electrochemical $NO_2$ sensor as a reference. All metal-oxide sensors showed reasonable responses in the ranges provided by their respective datasheets. The sensors showed responses at levels out of their specified ranges, but with low accuracy. Humidity changes affected the performance of metal-oxide sensors. Therefore, recalibration of the sensors should be performed to compensate for the humidity effects. In investigating the temperature effects, the sensor responses were significantly affected, which might be due to thermally-induced air turbulence on the sensing material. In applications where the space is small and heated by nearby high-temperature sources, this may be a source for sensor signal deviation. To resolve the variations due to the humidity and temperature changes in practical cases, a compensation circuit or software using a temperature and a humidity sensor is needed. Both sensors can be integrated along with the gas sensor. A block diagram to demonstrate the idea is shown in FIG. 17B.

The results of the selectivity tests showed that the $NO_2$ metal-oxide gas sensors are less affected by the presence of $O_2$ than by $CO_2$. Based on our results, provided that metal-oxide sensors have advantages of being small in sizes, low in costs and having long useful lifetimes, careful consideration should be exercised when choosing a sensor that will be suitable to a specific application.

The wireless sensor system is also suitable for integration of multi-modality sensors. Patch-type sensors, such as blood pressure sensors, pulse sensors, heart rate sensors, and clamp-type sensors, such as optical $pO_2$ sensors and glucose sensors can be included in the ports of the PCB. Each sensor, with its own ID, can be connected to the processing board with a wireless module. For this purpose, multiple channel information will require high data rates for quick transmission and response. A higher carrier frequency, such as 2.4 GHz, with more efficient modulation, such as Quadrature Phase-Shift Keying ('QPSK"), then is needed.

Phase-shift keying (PSK) is a digital modulation scheme that conveys data by changing, or modulating, the phase of a reference signal (the carrier wave). Any digital modulation scheme uses a finite number of distinct signals to represent digital data. PSK uses a finite number of phases; each assigned a unique pattern of binary bits. Usually, each phase encodes an equal number of bits. Each pattern of bits forms the symbol that is represented by the particular phase. The demodulator, which is designed specifically for the symbol-set used by the modulator, determines the phase of the received signal and maps it back to the symbol it represents, thus recovering the original data. This requires the receiver to be able to compare the phase of the received signal to a reference signal—such a system is termed coherent. QPSK uses four different phase angles, which are usually out of phase by 90°. With four phases, QPSK can encode two bits per symbol.

In one embodiment of the invention, an infant monitoring system 100 uses multiple $CO_2$ sensors. The infant monitoring system provides advantages such as lower costs, non-invasive sensing mechanism, and away-from-the-infant wireless transmission. The infant monitoring system is beneficial to caregivers and can prevent SIDS.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A wireless sensor system comprising:
   at least one sensor coupled to a Radio Frequency Identification system comprising a transmitter and a receiver, wherein the transmitter includes a wireless module and the transmitter is configured to transmit an alarm signal, the alarm signal being transmitted by the transmitter when the output from the sensor is lower than a specific threshold, and wherein the receiver triggers an alarm when the alarm signal is received;
   a circuit coupled to the sensor and the wireless module, wherein the circuit is configured to set a threshold voltage;
   further comprising a humidity sensor coupled to the circuit and a negative feedback loop configured to provide linear voltage output of the circuit versus percentage of relative humidity;
   a demultiplexer configured to separate the signals received by the receiver from the transmitter and at least one comparator coupled to the alarm; and
   a storage system configured to store a sensing signal received from the sensor, wherein the storage system is coupled to the receiver.

2. The wireless sensor system of claim 1, wherein the circuit further comprises at least one comparator configured to set the specific threshold.

3. The wireless sensor system of claim 1, wherein the transmitter further comprises a multiplexer; and the multiplexer multiplexes the signal from the sensor in the time domain.

4. The wireless sensor system of claim 1, wherein the transmitter further comprises an AND gate.

5. The wireless sensor system of claim 1, wherein the sensor is a gas sensor.

6. The wireless sensor system of claim 5, wherein the gas sensor is a metal-oxide sensor.

7. The wireless sensor system of claim 6, wherein the specific threshold is set to detect a condition.

8. The wireless sensor system of claim 7, wherein the specific threshold is set to detect sudden infant death syndrome.

9. The wireless sensor system of claim 1, further comprising a camera and a microphone.

10. The wireless sensor system of claim 1, further comprising a plurality of ports for a plurality of sensors.

11. The wireless sensor system of claim 1, wherein the sensor, the transmitter, and the receiver operate in an active Radio Frequency Identification system.

12. The wireless sensor system of claim 1, wherein the sensor, the transmitter, and the receiver operate in a passive Radio Frequency Identification system.

13. The wireless sensor system of claim 1, further comprising a reader collision system.

14. The wireless sensor system of claim 1, wherein the sensor includes an identification signal to correlate a sensing data signal and the alarm signal with the identification signal.

15. A wireless sensor system comprising:
   a. at least one sensor coupled to a Radio Frequency Identification system comprising a transmitter and a receiver, wherein the transmitter includes a wireless module and the transmitter is configured to transmit an alarm signal and a sensing signal;
   b. the alarm signal transmitted by wherein the transmitter is configured to transmit the alarm signal when the output from the sensor is lower than a specific threshold;
   c. wherein the receiver is configured to trigger an alarm when the alarm signal is received;
   d. a storage system configured to store a sensing signal received from the sensor, wherein the storage system is coupled to the receiver; and
   e. a humidity sensor coupled to the circuit and a negative feedback loop to provide linear voltage output of the circuit versus percentage of relative humidity.

16. The wireless sensor system of claim 15, further comprising a camera and a microphone.

* * * * *